United States Patent [19]

Engel et al.

[11] Patent Number: 4,600,773

[45] Date of Patent: Jul. 15, 1986

[54] CRYSTALLINE CEPHALEXIN HYDROCHLORIDE MONOHYDRATE

[75] Inventors: Gary L. Engel; Joseph M. Indelicato, both of Greenwood; Harry A. Rose, Indianapolis, all of Ind.

[73] Assignee: Eli Lilly and Company, Indianapolis, Ind.

[21] Appl. No.: 556,887

[22] Filed: Dec. 1, 1983

[51] Int. Cl.$^4$ .......................................... C07D 501/22
[52] U.S. Cl. ...................................................... 544/30
[58] Field of Search ...................................... 544/19, 30

[56] References Cited

U.S. PATENT DOCUMENTS

| | | | |
|---|---|---|---|
| 3,507,861 | 4/1970 | Morin et al. | 260/243 |
| 3,655,656 | 4/1972 | Van Heyningen | 260/243 C |
| 3,985,747 | 10/1976 | Kaplan et al. | 544/26 |
| 4,386,070 | 5/1983 | DeVincentiis | 424/114 |

FOREIGN PATENT DOCUMENTS 151890  4/1975  Japan .

OTHER PUBLICATIONS

Wheeler, et al., "Orally Active Esters of Cephalosporin Antibiotics," J. Med. Chem. (22) 657–661 (1979).
Page 91 of laboratory notebook of C. Ryan dated 8-7-67; plus page identifying Ryan compound and "61188".
Pfeiffer et al., *Crystal Pseudopolymorphism of Cephaloglycin and Cephalexin,* J. Pharm. Sci., vol. 59, No. 12, 1970 (1890–1814).
Pages 90 and 96, K. S. Yang laboratory notebook, dated Jun. 4, 1968 and Jul. 3, 1968 respectively.

*Primary Examiner*—Mark L. Berch
*Assistant Examiner*—G. Hendricks
*Attorney, Agent, or Firm*—Charles W. Ashbrook; Arthur R. Whale

[57] ABSTRACT

Crystalline cephalexin hydrochloride ethanol solvate converts to crystalline cephalexin hydrochloride monohydrate upon being exposed to moisture.

10 Claims, No Drawings

CRYSTALLINE CEPHALEXIN HYDROCHLORIDE MONOHYDRATE

BACKGROUND OF THE INVENTION

Cephalexin is the generic term used to identify the chemical compound 7-(D-α-aminophenylacetamido)-3-methyl-3-cephem-4-carboxylic acid. The compound is described in U.S. Pat. No. 3,507,861. While cephalexin is a potent antibacterial agent, it does not lend itself to convenient formulation for human therapy because of its physical characteristics. U.S. Pat. No. 3,655,656 describes a process for prreparing a unique form of cephalexin, namely a monohydrate, which is a highly crystalline dense form of cephalexin ideally suited to formulation into capsules and tablets for human therapy.

While cephalexin monohydrate has enjoyed widespread commercial success as a two to four times-a-day treatment for diseases of bacterial origin, it heretofore has not been possible to formulate it into a slow-release rate controlled drug form. It is now recognized that controlling the blood concentrations of a therapeutic agent such as cephalexin over a prolonged period of time is a method of improving the selectivity of the agents' beneficial actions. Moreover, a once or twice-a-day administration of a slow-release dosage form is much more convenient and preferred over the requirement of multiple dosings per day.

A technology involving concepts of an elementary osmotic pump recently has been developed and has proven to be effective in permitting control of drug content and rate of drug delivery in vivo; see Theeuwes, F., "Elementary Osmotic Pump," *J. Pharm. Sci.*, Vol. 64, 1975, pp 1987–1991. In order to function in such a delivery system, a pharmaceutical agent must be sufficiently soluble in water and body fluids to permit development of sufficient differential osmotic pressure to effect release of the active agent into the biological system being treated. The agent must also be of sufficient stability such that it retains its pharmacological potency throughout the entire release period, which may extend from about three to about twelve hours duration.

While cephalexin monohydrate is ideally suited to formulation into conventional dosage forms such as capsules and tablets, it does not lend itself to formulation as a controlled release dosage form employing the osmotic pump technology, primarily because of its relatively low water solubility and the consequent low osmotic pressure of its solutions. Moreover, the low solubility of cephalexin monohydrate delays its absorption so that high blood levels are not immediately realized following administration of conventional formulations.

An object of this invention is to provide a new chemical compound that is a crystalline form of the hydrochloride salt of cephalexin. The new compound has excellent solubility and osmotic pressure characteristics and is ideally suited to formulation as a controlled release dosage form employing the osmotic pump technology. The improved solubility of the compound of this invention permits immediate and improved blood levels following administration of conventional formulations thereof. Another object of the invention is to provide an intermediate that is important in the synthesis of the new compound. A further object of the invention is to provide a process for preparing the new composition of matter and a method for its use.

SUMMARY OF THE INVENTION

This invention concerns a crystalline form of the hydrochloride salt of cephalexin. The invention more particularly provides the monohydrate of cephalexin hydrochloride in crystalline form. The invention also provides a crystalline ethanol solvate of cephalexin hydrochloride, which is useful as an intermediate in the synthesis of cephalexin hydrochloride monohydrate. A further embodiment of the invention is a process for preparing crystalline cephalexin hydrochloride monohydrate which comprises exposing cephalexin hydrochloride ethanol solvate to an atmosphere having a relative humidity of about 10 to about 50%. Still another embodiment is a pharmaceutical formulation comprising cephalexin hydrochloride monohydrate and a method of treatment employing the compound.

DETAILED DESCRIPTION OF THE INVENTION

Since cephalexin contains a primary amino group in its side chain, it readily forms acid addition salts by reaction with organic and inorganic acids. For example, reaction of cephalexin with an acid such as trifluoroacetic acid provides cephalexin trifluoroacetate. Similarly, reaction of cephalexin with hydrochloric acid gives the hydrochloride salt. This invention provides a method for obtaining a stable crystalline form of a solvate of cephalexin hydrochloride.

The cephalexin hydrochloride monohydrate crystalline form provided by this invention is prepared by exposing cephalexin hydrochloride ethanol solvate to an atmosphere such as air having a relative humidity of about 10 to about 50 percent. The reaction appears to be an actual crystal transformation from crystalline ethanol solvate to crystalline monohydrate.

Cephalexin hydrochloride ethanol solvate is a new composition of matter provided as another embodiment of this invention. The ethanol solvate can be prepared by adding about an equimolar amount of hydrogen chloride or hydrochloric acid to an ethanolic suspension of cephalexin. The cephalexin hydrochloride ethanol solvate typically crystallizes out of solution, and such crystallization can be assisted by chilling or by addition of an antisolvent such as a hydrocarbon solvent or the like.

Cephalexin hydrochloride ethanol solvate is a stable crystalline material in the absence of water. The crystalline cephalexin hydrochloride ethanol solvate is a new composition of matter having the following unique X-ray powder diffraction properties when measured with a diffractometer having a nickel-filtered copper target tube of 1.5405 Å;

| Spacing, d(Å) | Relative Intensities, $I/I_1$ |
| --- | --- |
| 14.48 | 1.00 |
| 10.04 | .005 |
| 9.16 | .01 |
| 8.58 | .02 |
| 7.34 | .095 |
| 6.10 | .055 |
| 5.75 | .05 |
| 5.48 | .175 |
| 5.08 | .01 |
| 4.62 | .035 |
| 4.32 | .035 |

| Spacing, d(Å) | Relative Intensities, I/I$_1$ |
| --- | --- |
| 4.02 | .025 |
| 3.97 | .025 |
| 3.78 | .01 |
| 3.72 | .035 |
| 3.68 | .06 |
| 3.43 | .01 |
| 3.36 | .06 |
| 3.16 | .035 |
| 3.04 | .035 |
| 2.74 | .01 |
| 2.54 | .01 |
| 2.52 | .025 |
| 2.45 | .01 |
| 2.42 | .015 |

While the cephalexin hydrochloride ethanol solvate is relatively stable in the substantial absence of moisture, if it is exposed to an atmosphere having a relative humidity greater than about 10% the ethanol solvate is unstable and is converted to the monohydrate crystalline form of this invention. The rate of conversion varies depending upon the particle size of the ethanol solvate and the relative humidity to which it is exposed. If the ethanol solvate intermediate is subjected to an atmosphere of greater than about 70% relative humidity, the cephalexin hydrochloride does not form the monohydrate crystalline structure provided by this invention, but instead becomes an amorphous mass that fails to crystallize.

In a preferred embodiment, the ethanol solvate is exposed to air having relative humidity of about 20 to about 45%, at a temperature of about 20° to about 50° C., and under such conditions conversion to the hydrochloride monohydrate crystalline form of this invention is substantially complete after about one to about fourteen days.

The crystalline cephalexin hydrochloride monohydrate of this invention has the following unique X-ray powder diffraction properties when measured with a 114.6 mm Debye-Scherrer camera using nickel-filtered copper target tube of 1.5418 Å.

| Spacing, d: | Relative intensities, I/I$_1$ |
| --- | --- |
| 14.03 | 1.00 |
| 7.08 | .33 |
| 5.42 | .33 |
| 4.63 | .73 |
| 4.41 | .27 |
| 4.31 | .13 |
| 4.17 | .47 |
| 3.99 | .13 |
| 3.78 | .40 |
| 3.70 | .27 |
| 3.55 | .53 |
| 3.38 | .20 |
| 3.21 | .07 |
| 3.12 | .07 |
| 3.03 | .07 |
| 2.85 | .13 |
| 2.73 | .03 |
| 2.65 | .03 |
| 2.59 | .03 |
| 2.53 | .13 |
| 2.37 | .20 |
| 2.29 | .13 |
| 2.18 | .03 |
| 2.14 | .03 |
| 1.996 | .13 |
| 1.959 | .07 |

The cephalexin hydrochloride monohydrate crystalline form of this invention is unusually soluble in water, forming a saturated aqueous solution containing 766 mg per ml of distilled water at 37° C. The pH of such solution is about 0.5. This solution exhibits an osmotic pressure at 143 atm. This is to be contrasted with cephalexin monohydrate which has a solubility of only 12.6 mg per ml of distilled water, and which solution exhibits a pH of 3.2 and an osmotic pressure of only 1.5 atm. While the sodium salt of cephalexin is a relatively soluble material (552 mg/ml in distilled water, pH of this solution is 8.9, osmotic pressure is 117 atm.) it is unacceptable for a sustained release dosage form because it rapidly degrades in solution and would not be stable for more than about two hours at ambient temperatures.

The cephalexin hydrochloride monohydrate crystalline form provided by this invention is useful as an orally active antibacterial agent, and is particularly well suited to pharmaceutical formulation. The compound can be admixed with conventional carriers and excipients such as sucrose, polyvinylpyrrolidone, stearic acid, starch and the like and encapsulated, or if desired the formulation can be compressed into tablets. A preferred embodiment is a tablet that can be administered to an animal and that provides for substantially immediate release of the active ingredient into the biological system. Such pharmaceutical formulations will contain from about 10 to about 98% by weight of active ingredient, for example from about 200 to about 1200 mg of active ingredient, and will be administered to a human subject at the rate of one or more doses each day for the control and prevention of diseases caused by bacteria. The compound can additionally be admixed with polymers made from polymerizable materials such as methacrylate esters, glycols, hydroxy acids such as lactic acid and the like, and molded into tablets or the like which are suitable controlled release formulations.

While the cephalexin hydrochloride monohydrate crystalline form can be formulated for oral administration employing conventional encapsulation and tableting technology, it is also well suited to formulation as a controlled release dosage form, especially employing osmotically actuated technology for rate-controlled drug delivery. For a compound to be suitable for delivery via an osmotic pump, it must be sufficiently soluble in water or similar fluid to be solubilized over a period of time sufficiently long to provide continuous delivery over a desired period at pharmacologically effective rates, and sufficiently stable when in solution to remain therapeutically efficacious over the entire period of administration. The compound of this invention uniquely satisfies these requirements of solubility, osmotic pressure and stability. Moreover, the cephalexin hydrochloride monohydrate crystalline structure of this invention is in a pharmaceutically acceptable state of purity in that the level of alkanol contaminant generally is less than about one percent by weight. The novel monohydrate polymorph of this invention is produced by the process of the invention in a state of purity greater than about 98 percent by weight.

The preparation of osmotically driven delivery systems is well documented in the prior art. U.S. Pat. Nos.

3,845,770, 3,977,404, 4,008,719, 4,014,334, 4,016,880, 4,034,758, 4,036,227, 4,036,228, 4,096,238, 3,916,899, 4,111,203, 4,116,241, 4,160,020 4,200,098 and 4,210,139 disclose typical methods for preparing and using osmotic delivery systems, and are incorporated herein by reference for that teaching.

The amount of cephalexin hydrochloride monohydrate that is present in the osmotically-driven delivery device is not critical but typically is an amount that is equal to or larger than the amount that is necessary to osmotically operate the device for the desired period of drug release such that the desired therapeutic level of active agent is achieved for the desired period of time. A preferred osmotically-driven controlled release formulation is one that delivers an efficacious amount of cephalexin hydrochloride monohydrate over about four to about six hours or longer.

A further embodiment of this invention is a method of treating bacterial infections in animals such as humans comprising administering an antibacterially effective amount of the cephalexin hydrochloride monohydrate crystal form of this invention. Since the compound is prepared from cephalexin hydrochloride ethanol solvate, some residual ethanol might be present in the monohydrate. Generally ethanol will not be present in the monohydrate crystalline form in an amount greater than about one percent by weight, and such amount is not detrimental to a biological system.

The amount of cephalexin hydrochloride monohydrate that is antibacterially effective is about 1 to about 30 mg/kg of animal body weight. Ideally a subject will receive a dose of about 3 to about 10 mg/kg once a day, or more often as needed to effectively treat or prevent the infection afflicting the subject. While cephalexin hydrochloride monohydrate will display an activity profile very similar to that of cephalexin monohydrate, it is expected that higher blood levels and a more rapid onset of action will be enjoyed with cephalexin hydrochloride monohydrate than with the current commercial cephalexin monohydrate, due to its unusually greater solubility. Indeed, the compound of the invention is ideally suited to formulation as an immediate release tablet composition.

The practice of the present invention is further illustrated by the following detailed examples, none of which are to be construed as limiting the invention in any respect.

EXAMPLE 1

Cephalexin hydrochloride ethanol solvate

Cephalexin monohydrate (100 g) was suspended in 300 ml of absolute ethanol. The suspension was stirred at 25° C. while hydrogen chloride was bubbled through the suspension until all particles were in solution. The reaction mixture was stirred at 25° C. for two hours, and then cooled to 0° C. and stirred for an additional two hours. The crystalline product was collected by filtration and washed with 200 ml of 1:1 (v/v) ethanol-ethyl acetate and then with 200 ml of ethyl acetate. The product was identified as cephalexin hydrochloride ethanol solvate. Yield 53 grams.

NMR: ($D_2O$): $\delta$1.2 (t, 3H); $\delta$2.02 (s, 1H); $\delta$3.23 (q, 2H); $\delta$3.65 (q, 2H); $\delta$5.0 (d, 1H); $\delta$5.3 (s, 1H); $\delta$5.61 (d, 1H); $\delta$7.59 (s, 5H).

EXAMPLE 2

Cephalexin hydrochloride monohydrate

To a stirred suspension of 45 kg of cephalexin monohydrate in 168 liters of absolute ethanol were added portion-wise over thirty minutes 5.7 kg of hydrogen chloride. The reaction mixture was stirred at 25° C. for thirty minutes, and then was cooled to 10° C. and stirred for an additional two hours. The crystalline precipitate that had formed was collected by filtration and washed with 24 liters of 1:1 (v/v) ethanol-hexane, and finally with 22 liters of hexane. The filter cake was shown by NMR to be cephalexin hydrochloride ethanol solvate (NMR consistent with that reported in Example 1).

Elemental Analysis calculated for ethanol solvate: $C_{16}H_{17}N_3O_4S \cdot HCl \cdot CH_3CH_2OH$: Theory: C, 50.29; H, 5.63; N, 9.77; S, 7.46; Cl, 8.25; Found: C, 50.03; H, 5.45; N, 9.84; S, 7.35; Cl, 8.37.

The ethanol solvate filter cake from above was exposed for two weeks to an atmosphere of air of about 35% relative humidity at a temperature of about 25°–30° C. to provide 31.76 kg of cephalexin hydrochloride monohydrate.

NMR ($D_2O$): $\delta$2.06 (s, 3H); $\delta$3.30 (q, 2H); $\delta$5.0 (d, 1H); $\delta$5.32 (s, 1H); $\delta$5.68 (d, 1H); $\delta$7.61 (s, 5H).

IR (KBr): 3290 cm$^{-1}$; 3120 cm$^{-1}$; 1760 cm$^{-1}$; 1710 cm$^{-1}$; 1680 cm$^{-1}$; 1560 cm$^{-1}$; 1490 cm$^{-1}$.

Karl Fisher water analysis: 4.48% (n=4), consistent with the presence of approximately one mole of water. Residual ethanol determined to be 0.68%.

Elemental Analysis Calculated for cephalexin hydrochloride monohydrate: $C_{16}H_{17}N_3O_4S \cdot HCl \cdot H_2O$; Theory: C, 47.82; H, 5.02; N, 10.46; S, 7.98; Cl, 8.82. Found: C, 48.03; H, 4.82; N, 10.27; S, 7.87; Cl, 8.90.

Differential thermal analysis demonstrated the compound has a large broad endotherm at 109° C. which appears to indicate a loss of volatile materials, and a sharp exotherm at 202° C. which appears to indicate decomposition of the compound. A thermal gravimetric analysis showed a weight loss beginning at 63° C. which resulted in a 5.7% weight loss at 135° C. At 150° C. another weight loss began and continued through decomposition. The compound demonstrated an X-ray powder diffraction pattern consistent with that reported above for cephalexin hydrochloride monohydrate.

EXAMPLE 3

The effect of humidity on the rate of change of cephalexin hyrochloride ethanol solvate to cephalexin hydrochloride monohydrate was studied by X-ray diffraction of samples of the ethanol solvate after storage at 25° C. in chambers of different relative humidities. The change from ethanol solvate to monohydrate was followed by observing the disappearance of an X-ray maximum having a d value of about 7.34 Å. The 7.34 results of the study are presented in Table I.

TABLE I

| | Disappearance of 7.34Å X-Ray Maximum with Time at Various Humidities at 25° C. | | | |
|---|---|---|---|---|
| | Relative Humidity (%) | | | |
| Time | 0 | 20 | 32 | 44 |
| 0 hours | 19 units | 19 units | 19 units | 19 units |
| 24 | 18 | 10 | 7 | 2 |
| 48 | 17 | 8 | 5 | 1 |
| 72 | — | 6 | 4 | — |
| 144 | — | 4 | 2 | 0 |
| 260 | — | 2 | 1 | — |

TABLE I-continued

Disappearance of 7.34Å X-Ray Maximum
with Time at Various Humidities at 25° C.

| Time | Relative Humidity (%) | | | |
|---|---|---|---|---|
| | 0 | 20 | 32 | 44 |
| 888 | — | 1 | 0 | — |

Note: "—" means that no reading was taken.

A sample of the ethanol solvate held at 70% relative humidity was totally dissolved within twenty-four hours.

EXAMPLE 4

Stability of Cephalexin Hydrochloride monohydrate

A sample of cephalexin hydrochloride monohydrate from Example 2 was analyzed by high pressure liquid chromatography and shown to contain 84.6% cephalexin.

(This is equivalent to a purity of about 99.2% for the cephalexin hydrochloride monohydrate, the remainder being substantially all ethanol) Samples of this material were stored at various temperatures for a prolonged period of time. The samples were assayed periodically by high pressure liquid chromatography (HPLC) and by Karl Fischer (KF) titration. The results of the study are given in the following Table II:

TABLE II

Stability of bulk Cephalexin hydrochloride monohydrate

| Time of assay | 5° C.* | | | 25° C. | | | 40° C. | | | 50° C. | | |
|---|---|---|---|---|---|---|---|---|---|---|---|---|
| | HPLC | KF | Total | HPLC | KF | Total | HPLC | KF | Total | HPLC | KF | Total |
| inital | 84.01 | 5.58 | 89.59 | 84.01 | 5.58 | 89.59 | 84.01 | 5.58 | 89.59 | 84.01 | 5.58 | 89.59 |
| 1.5 mo. | 81.42 | 6.28 | 87.70 | 84.01 | 5.66 | 89.67 | 84.46 | 5.47 | 89.93 | 85.06 | 5.50 | 90.56 |
| 3 mo. | 80.34 | 5.25 | 85.59 | 84.42 | 4.81 | 89.23 | 83.74 | 4.70 | 88.44 | 84.41 | 4.63 | 89.04 |
| 6 mo. | 78.86 | 5.60 | 87.40 | 86.52 | 4.23 | 90.75 | 86.45 | 4.14 | 90.59 | 86.34 | 4.38 | 90.72 |
| 9 mo. | 80.95 | 6.20 | 87.15 | 84.10 | 5.28 | 84.38 | 83.82 | 5.11 | 88.93 | 83.16 | 5.19 | 88.35 |
| 12 mo. | 77.77 | 9.07 | 86.84 | 83.33 | 6.97 | 90.30 | 84.66 | 4.81 | 89.47 | 83.83 | 4.71 | 88.54 |

*This sample was placed in a plastic container permeable to moisture and stored in a refrigerator in which the atmosphere was quite moist. It is believed that this constant exposure to high humidity contributed to the observed decomposition and increase in water content.

The above data demonstrates that cephalexin hydrochloride monohydrate is quite stable over long periods of time and over a wide temperature range when maintained in an atmosphere of low moisture content.

Another sample of the compound of Example 2 was held at 40° C. in a tightly closed metal container having an atmosphere of 75% relative humidity. The results of this study are presented below in Table III.

TABLE III

Stability of cephalexin hydrochloride monohydrate
at 40° C. and 75% relative humidity

| | HPLC | KF | Total |
|---|---|---|---|
| Initial | 84.01 | 5.5 | 89.59 |
| 1 month | 83.18 | 5.51 | 88.69 |
| 3 months | 78.71 | 4.97 | 83.68 |
| 6 months | 61.88 | 5.62 | 67.50 |
| 9 months | 51.34 | 6.42 | 57.76 |

This study shows that cephalexin hydrochloride monohydrate is stable for about one month at 40° C. and 75% relative humidity. Prolonged storage under high moisture conditions leads to decomposition.

EXAMPLE 5

| Tablet for Immediate Release Product | |
|---|---|
| Ingredient | Amount |
| Cephalexin hydrochloride monohydrate of Example 2 (850 mcg cephalexin/mg) | 617.7 mg |
| Povidone | 12.6 mg |
| Carboxymethylcellulose Sodium (Cross Linked) | 26.0 mg |
| Stearic Acid | 12.6 mg |
| Magnesium Stearate | 6.3 mg |

The cephalexin hydrochloride monohydrate were granulated with povidone in dichloromethane. After drying and sizing, the granules were blended to uniformity with the remaining ingredients and compressed. The tablets may be coated with hydroxypropyl methyl cellulose and a plasticiser in a suitable organic solvent system. The tablets effect an immediate release of active ingredient following administration to a subject.

EXAMPLE 6

| Tablet Formulation | |
|---|---|
| Ingredient | Amount |
| Cephalexin hydrochloride monohydrate (Example 2) | 617.7 mg |
| Povidone | 12.6 mg |
| Emcosoy ® (excipient derived from defatted soybeans; Edward Mendell Co., Inc.) | 26.0 mg |
| Stearic Acid | 12.6 mg |
| Magnesium Stearate | 6.3 mg |

The above ingredients were blended as described in Example 5 and compressed into tablets. The tablets are administered to humans and provide a substantially immediate release of antibiotic substance.

EXAMPLE 7

| Ingredient | Amount |
|---|---|
| Cephalexin hydrochloride monohydrate (Example 2) | 617.7 mg |
| Povidone | 12.6 mg |
| Starch | 26.0 mg |
| Stearic Acid | 12.6 mg |
| Magnesium Stearate | 6.3 mg |

The ingredients were blended by the method described in Example 5. The resulting tablets were coated with hydroxypropyl methyl cellulose for use as immediate release antibacterial pharmaceutical form.

EXAMPLE 8

| Capsule formulation | |
|---|---|
| Ingredient | Amount |
| Cephalexin hydrochloride monohydrate | 450 mg |
| Povidone | 10 mg |
| Magnesium Stearate | 5 mg |

The ingredients were blended to uniformity and placed into an elongated gelatin capsule. The capsule will be orally administered for the rapid control of bacterial infections.

We claim:

1. Crystalline cephalexin hydrochloride ethanol solvate exhibiting essentially the following X-ray diffraction data:

| Spacing, d(Å) | Relative Intensities, $I/I_1$ |
|---|---|
| 14.48 | 1.00 |
| 10.04 | .005 |
| 9.16 | .01 |
| 8.58 | .02 |
| 7.34 | .095 |
| 6.10 | .055 |
| 5.75 | .05 |
| 5.48 | .175 |
| 5.08 | .01 |
| 4.62 | .035 |
| 4.32 | .035 |
| 4.02 | .025 |
| 3.97 | .025 |
| 3.78 | .01 |
| 3.72 | .035 |
| 3.68 | .06 |
| 3.43 | .01 |
| 3.36 | .06 |
| 3.16 | .035 |
| 3.04 | .035 |
| 2.74 | .01 |
| 2.54 | .01 |
| 2.52 | .025 |
| 2.45 | .01 |
| 2.42 | .015 |

2. Crystalline cephalexin hydrochloride monohydrate exhibiting essentially the following X-ray diffraction data:

| Spacing, d(Å) | Relative Intensities $I/I_1$ |
|---|---|
| 14.03 | 1.00 |
| 7.08 | .33 |
| 5.42 | .33 |
| 4.63 | .73 |
| 4.41 | .27 |
| 4.31 | .13 |
| 4.17 | .47 |
| 3.99 | .13 |
| 3.78 | .40 |
| 3.70 | .27 |
| 3.55 | .53 |
| 3.38 | .20 |
| 3.21 | .07 |
| 3.12 | .07 |
| 3.03 | .07 |
| 2.85 | .13 |
| 2.73 | .03 |
| 2.65 | .03 |
| 2.59 | .03 |
| 2.53 | .13 |
| 2.37 | .20 |
| 2.29 | .13 |
| 2.18 | .03 |
| 2.14 | .03 |
| 1.996 | .13 |
| 1.959 | .07 |

3. A process for preparing the cephalexin hydrochloride monohydrate of claim 2 which comprises exposing cephalexin hydrochloride ethanol solvate to an atmosphere having a relative humidity of about 10% to about 50%.

4. The process of claim 3 wherein the relative humidity is about 15 to about 45%.

5. The process of claim 3 wherein the relative humidity is about 20 to about 40%.

6. A pharmaceutical formulation comprising the cephalexin hydrochloride monohydrate of claim 2 together with a pharmaceutical excipient, diluent or carrier therefor.

7. The formulation of claim 6 in the form of a tablet.

8. The formulation of claim 6 in the form of a capsule.

9. A method of treating bacterial infections comprising administering to a subject an antibacterial amount of the compound of claim 2.

10. The method of claim 9 employing a tablet formulation.

* * * * *